(12) United States Patent
Sharma et al.

(10) Patent No.: US 12,059,393 B2
(45) Date of Patent: Aug. 13, 2024

(54) COMPOSITIONS FOR TOPICAL TREATMENT OF RADIATION DERMATITIS

(71) Applicant: Akos Biosciences, Inc, Naples, FL (US)

(72) Inventors: Purnendu Kumar Sharma, Cary, NC (US); Alon Mantel, Cary, NC (US); Srikanth Manne, Cary, NC (US); Vijendra Nalamothu, Raleigh, NC (US); Ramanathan Lalgudi, Westerville, OH (US)

(73) Assignee: AKOS BIOSCIENCES, INC., Naples, FL (US)

( * ) Notice: Subject to any disclaimer, the term of this patent is extended or adjusted under 35 U.S.C. 154(b) by 0 days.

(21) Appl. No.: 17/982,909

(22) Filed: Nov. 8, 2022

(65) Prior Publication Data

US 2023/0255900 A1 Aug. 17, 2023

Related U.S. Application Data

(60) Provisional application No. 63/390,933, filed on Jul. 20, 2022, provisional application No. 63/321,281, filed on Mar. 18, 2022, provisional application No. 63/309,194, filed on Feb. 11, 2022.

(51) Int. Cl.

| | | |
|---|---|---|
| *A61K 31/277* | (2006.01) |
| *A61K 9/00* | (2006.01) |
| *A61K 9/107* | (2006.01) |
| *A61K 31/05* | (2006.01) |
| *A61K 31/343* | (2006.01) |
| *A61K 31/352* | (2006.01) |
| *A61K 31/353* | (2006.01) |
| *A61K 47/10* | (2017.01) |
| *A61K 47/12* | (2006.01) |
| *A61K 47/26* | (2006.01) |
| *A61K 47/44* | (2017.01) |
| *A61P 17/00* | (2006.01) |

(52) U.S. Cl.
CPC ............ *A61K 31/05* (2013.01); *A61K 9/0014* (2013.01); *A61K 9/107* (2013.01); *A61K 31/343* (2013.01); *A61K 31/352* (2013.01); *A61K 31/353* (2013.01); *A61K 47/10* (2013.01); *A61K 47/12* (2013.01); *A61K 47/26* (2013.01); *A61K 47/44* (2013.01); *A61P 17/00* (2018.01)

(58) Field of Classification Search
None
See application file for complete search history.

(56) References Cited

U.S. PATENT DOCUMENTS

| | | | |
|---|---|---|---|
| 9,549,906 B2 | 1/2017 | Lynch | |
| 10,238,745 B2 | 3/2019 | Finley | |
| 10,765,713 B2 | 9/2020 | Walser | |
| 2004/0110827 A1 | 6/2004 | Aviv | |
| 2016/0120803 A1 | 5/2016 | Mathur | |
| 2019/0151232 A1 | 5/2019 | Scharp | |
| 2019/0247299 A1 | 8/2019 | Cameron | |
| 2019/0255014 A1 | 8/2019 | Gardner | |
| 2020/0170950 A1 | 6/2020 | Adair | |
| 2020/0281998 A1* | 9/2020 | Scharp | ..................... A61Q 3/00 |
| 2020/0345657 A1* | 11/2020 | Lurya | ..................... A61K 36/21 |
| 2021/0052511 A1 | 2/2021 | Callahan et al. | |
| 2021/0113490 A1* | 4/2021 | Le Devedec | ........... A61P 17/10 |

FOREIGN PATENT DOCUMENTS

| | | |
|---|---|---|
| JP | 2020508994 A | 3/2020 |
| WO | 2017/027553 A1 | 2/2017 |
| WO | 2019/144190 A1 | 8/2019 |
| WO | 2019/234743 A1 | 12/2019 |
| WO | 2020/018512 A1 | 1/2020 |
| WO | 2020024056 A1 | 2/2020 |
| WO | 2020053857 A1 | 3/2020 |
| WO | 2021030190 A1 | 2/2021 |

OTHER PUBLICATIONS

Msalilwa etal., "Physicochemical Properties, Fatty Acid Composition, and the Effect of Heating on the Reduction of Cyclopropenoid Fatty Acids on Baobab (*Adansonia digitata* L.) Crude Seed Oil," J Lipids. Dec. 14, 2020. (Year: 2020).*
International Search Report of Application No. PCT/US2022/037748 Dated Nov. 3, 2022.
https://www.rasasvadabotanics.com/products/cbd-salve-900mg-original/ (Nov. 2019).
Msalilwa, et al., "Physicochemical Properties, Fatty Acid Composition and the Effect of Heating on the Reduction of Cyclopropenoid Fatty Acids on Baobab (*Adansonia digitata* L.) Crude Seed Oil," J Lipids. Dec. 14, 2020.
International Search Report of Application No. PCT/US2023/012482 Dated May 22, 2023.

* cited by examiner

*Primary Examiner* — Layla Soroush
(74) *Attorney, Agent, or Firm* — Lippes Mathias LLP (57) ABSTRACT

The present disclosure relates to topical compositions and methods for the treatment of radiation dermatitis. The compositions include specific formulations of a cannabinoid and olive oil, along with other specified ingredients.

16 Claims, 5 Drawing Sheets

COMPOSITIONS FOR TOPICAL TREATMENT OF RADIATION DERMATITIS

CROSS-REFERENCE TO RELATED APPLICATIONS

This application claims priority to U.S. Provisional Patent Application Ser. No. 63/390,933, filed on Jul. 20, 2022, and to U.S. Provisional Patent Application Ser. No. 63/321,281, filed on Mar. 18, 2022, and to U.S. Provisional Patent Application Ser. No. 63/309,194, filed on Feb. 11, 2022, each of which is incorporated by reference in its entirety.

BACKGROUND

The present disclosure relates to compositions, treatments, and methods for treating a patient with radiation dermatitis. This is done by administering, in therapeutically effective amounts, specific compositions comprising a cannabinoid and olive oil. In some embodiments, the olive oil contains at least 0.1 wt % of a cyclopropene fatty acid or cyclopropane fatty acid (CPFA).

Radiation treatment is used to treat malignancies, and is also used during interventional procedures such as coronary angiography, embolization procedures, and indwelling catheter placements. Of particular interest to doctors engaged in radiation therapy is the occurrence and management of radiation dermatitis, which is also known as radiodermatitis, x-ray dermatitis, radiation skin damage, or a radiation burn. Radiation dermatitis is a side effect of external beam ionizing radiation, commonly applied for example during treatments for cancer and other disorders. The radiation can deposit energy at the surface of the skin or several centimeters below the skin surface, depending on where the maximum dose is deposited.

Radiation dermatitis generally manifests within a few days to weeks after the start of radiotherapy. Symptoms can include changes ranging from faint erythema (reddening) during the first 2 weeks of treatment before progressing to desquamation (peeling skin) to skin necrosis (death of skin cells) and ulceration, depending on the severity of the reaction. Other changes in the skin can include the disappearance of follicular structures (pores); an increase in collagen and damage to elastic fibers in the dermis; a fragile surface skin (epidermis); and telangiectasia (prominent blood vessels).

Current treatments for radiation dermatitis include washing the affected skin with a gentle non-soap cleanser and drying with a soft, clean towel before each irradiation session. Emollients, moisturizers, gels, emulsions, and dressings, for example Aquaphor® or Eucerin®, can be applied after treatment and may reduce discomfort. Topical corticosteroids are also sometimes prescribed for radiation dermatitis for 2 to 4 weeks.

BRIEF DESCRIPTION

There remains a medical need for additional safer and more efficient formulations for the treatment and management of radiation dermatitis. Disclosed in various embodiments herein are specific, effective topical pharmaceutical formulations which comprise specific combinations of a cannabinoid and olive oil. In other embodiments, the olive oil also contains at least 0.1 wt % of a molecule containing an aliphatic chain with a cyclopropyl or cyclopropenyl group, such as a cyclopropene fatty acid or cyclopropane fatty acid (CPFA). Methods for the treatment of radiation dermatitis using such formulations and compositions are also described herein.

These and other non-limiting aspects of the disclosure are more particularly set forth below.

BRIEF DESCRIPTION OF THE DRAWINGS

The following is a brief description of the drawings, which are presented for the purposes of illustrating the exemplary embodiments disclosed herein and not for the purposes of limiting the same.

DETAILED DESCRIPTION

The present disclosure may be understood more readily by reference to the following detailed description of desired embodiments and the examples included therein. In the following specification and the claims which follow, reference will be made to a number of terms which shall be defined to have the following meanings.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

The singular forms "a," "an," and "the" include plural referents unless the context clearly dictates otherwise.

The term "comprising" is used herein as requiring the presence of the named ingredients/components/steps and allowing the presence of other ingredients/components/steps. The term "comprising" should be construed to include the term "consisting of", which allows the presence of only the named ingredients/components/steps. The term "consisting essentially of" should be construed to require the presence of the named ingredients/components/steps, and also permit the presence of other ingredients/components/steps that do not materially affect the basic and novel characteristics of the composition. For purposes of this disclosure, the basic and novel characteristics of the composition are its ability to treat radiation dermatitis.

Numerical values should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams to 10 grams" is inclusive of the endpoints, 2 grams and 10 grams, and all the intermediate values). The endpoints of the ranges and any values disclosed herein are not limited to the precise range or value; they are sufficiently imprecise to include values approximating these ranges and/or values.

The modifier "about" as used in this disclosure refers to plus or minus 10% of the indicated number. For example, "about 10%" may indicate a range of 9% to 11%, and "about 1" may mean from 0.9 to 1.1.

The term "up to X" is used in this disclosure to indicate an amount of an ingredient. This term should be construed to require the ingredient to be present in an amount greater than zero, or in other words to exclude the value zero.

The term "room temperature" means a temperature from 20° C. to 25° C.

The phrase "therapeutically effective amount" means a sufficient amount of the named ingredient to treat disorders, at a reasonable benefit/risk ratio applicable to any medical treatment. It will be understood, however, that the total daily usage of the compositions of the present disclosure will be decided by the attending physician or other care provider within the scope of sound medical judgment. The specific therapeutically effective dose level for any particular patient will depend upon a variety of factors, including the disorder being treated and the severity of the disorder; medical history of the patient, age, body weight, general health, sex and diet of the patient, the time of administration, route of administration, the duration of the treatment, other drugs being taken by the patient, and the like. A single administration may be sufficient to produce a therapeutic effect, but it is contemplated that multiple administrations will be used over a substantial period of time to assure continued response.

The present disclosure relates to compositions and methods for the treatment of dermatological conditions, especially radiation dermatitis which may arise after exposure to radiation, whether intentional (e.g. during medical treatment) or un-intentional. The compositions may also be useful in the treatment of various other medical conditions, such as for pain management, or for inflammatory conditions. The compositions are intended to be applied topically. The compositions include specified amounts of (A) a cannabinoid; and (B) olive oil as a carrier or solubilizer for the cannabinoid. In further embodiments, the compositions also include (C) an emulsifier; (D) diethylene glycol monoethyl ether; (E) polysorbate 80; (F) a gelling agent; (G) a fatty alcohol; and (H) water.

Cannabinoid

The compositions of the present disclosure include (A) a cannabinoid, which is non-psychoactive. A cannabinoid is a compound derived from the cannabis plant, also known as cannabis or hemp. Over 60 different cannabinoids are known to be naturally present in the cannabis plant. Cannabinoids can also be found in other plants such as, without limitation, rhododendron, licorice, liverwort, echinacea, clove, black pepper, broccoli, ginseng carrots, sunflowers, electric daisy, kava, tea plants, cacao, and black truffles. Cannabinoids can also be synthetically produced and are commercially available, for example from PureForm Global (Los Angeles, California). Synthetic cannabinoids which bind to the $CB_1$ receptor are also known, such as benzoylindoles, cyclohexylphenols, naphthoylindoles, and phenylacetylindoles. Some non-limiting examples of cannabinoids include cannabigerolic acid, cannabigerol, cannabinols, and cannabidiols.

The cannabinoid can be any cannabinoid or derivative thereof. For example, the cannabinoid can be a cannabidiol, cannabigerol, cannabichromene, tetrahydrocannabinol, cannabicyclol, cannabielsoin, cannabinol, cannabinodiol, cannabitriol, dehydrocannabifuran, cannabifuran, cannabichromanon, or cannabiripsol.

Examples of cannabidiols include cannabidiolic acid (CBDA), cannabidiol (CBD), cannabidiol monomethylether (CBDM), cannabidiol-C4 (CBD-C4), cannabidivarinic acid (CBDVA), cannabidivarin (CBDV), and cannabidiorcol (CBD-Ci).

Examples of cannabigerols include cannabigerolic acid (CBGA), cannabigerolic acid monomethylether (CBGAM), cannabigerol (CBG), cannabigerol monomethyleither (CBGM), cannabigerovarinic acid (CBGVA), and cannabigerovarin (CBGV).

Examples of cannabichromenes include cannabichromenic acid (CBC), cannabichromene (CBC), cannabichromevarinic acid (CBCVA), and cannabichromevarin (CBCV).

Examples of tetrahydrocannabinols include D-9-tetrahydrocannabinolic acid A (THCA-A), D-9-tetrahydrocannabinolic acid B (THCA-B), D-9-tetrahydrocannabinol (THC), D-9-tetrahydrocannabinolic acid-C4 (THCA-C4), A-9-tetrahydrocannabinol-C4 (THC-C4), D-9-tetrahydrocannabivarinic acid (THCVA), D-9-tetrahydrocannabivarin (THCV), D-9-tetrahydrocannabiorcolic acid (THCA-Ci), D-9-tetrahydrocannabiorcol (THC-Ci), D-7-cis-tetrahydrocannabivarin, D-8-tetrahydrocannabinolic acid ($A^8$-THCA), and D-8-tetrahydrocannabinol ($A^8$-THC).

Examples of cannabicyclols include cannabicyclolic acid (CBLA), cannabicyclol (CBL), and cannabicyclovarin (CBLV).

Examples of cannabielsoins include cannabielsoic acid A (CBEA-A), cannabielsoic acid B (CBEA-B), and cannabielsoin (CBE).

Examples of cannabinols and cannabinodiols include cannabinolic acid (CBNA), cannabinol (CBN), cannabinol-C4 (CBN-Cr), cannabivarin (CBV), cannabinol-C2 (CBN-C2), cannabiorcol (CBN-Ci), cannabinodiol (CBND), and cannabinodivarin (CBVD).

Examples of cannabitriols include cannabitriol (CBT), 10-ethoxy-9-hydroxy-A-6a-tetrahydrocannabinol, cannabitriolvarin (CBTV), and ethoxy-cannabitriolvarin (CBTYE).

Cannabifurans include dehydrocannabifuran (DCBF) and cannabifuran (CBF).

Examples of other cannabinoids include cannabichromanon (CBCN), 10-oxo-A-6a-tetrahydrocannabinol (OTHC), cannabiripsol (CBR), and trihydroxy-D-9-tetrahydrocannabinol (triOH-THC).

Derivatives of such cannabinoids may be used as well. For example, the hydroxyl, methyl, and olefinic groups can be modified to enhance binding affinity to cannabinoid receptors CB1 or CB2. For example, the groups may be modified through acetylation, methylation, or neutralization to form salts. Examples of such derivatives are illustrated in structures (CM-1) through (CM-5):

(CM-1)

The hydroxyl groups in derivatives (CM-1) and (CM-2) are acetylated, and (CM-2) is also carboxylated. The hydroxyl groups in derivative (CM-3) have been methylated. The sodium and potassium salts of CBD are illustrated in derivatives (CM-4) and (CM-5). Other salts, such as lithium or cesium, are also contemplated.

In particular embodiments, the cannabinoid is a cannabidiol or a cannabidiol derivative. As used herein, the terms "cannabidiol" and "CBD" are intended to refer to the compound 2-[(1R,6R)-6-Isopropenyl-3-methylcyclohex-2-en-1-yl]-5-pentylbenzene-1,3-diol, which is also designated as CAS #13956-29-1. CBD is a major non-psychoactive constituent of cannabis, in contrast to delta-9-tetrahydrocannabinol (THC) which is limited in therapeutic applications due to its psychoactive effects.

CBD can be provided as "full-spectrum CBD," "broad spectrum CBD," or "CBD isolate."

"Full-spectrum CBD" includes cannabinoids, terpenes, and flavonoids, as well as other less plentiful components (sterols, thiols, phenols, lipids or waxes, and fibrous materials). Full-spectrum CBD from cannabis includes CBD and THC as well as more than 100 minor cannabinoids present in small amounts; more than 150 terpenes which affect the plant's fragrance; and about 20 different flavonoids. Full-spectrum CBD can contain up to 0.3% THC.

In comparison, "broad-spectrum CBD" includes the same ingredients as full-spectrum CBD, except THC has been specifically removed. "CBD isolate" is only CBD. These materials can be provided in liquid form or powder form, and can be produced using conventional manufacturing processes.

It is noted that both CBD and THC are derived from cannabigerol (CBG), which itself is a cannabinoid and is one of the higher concentration constituents of full-spectrum CBD and broad-spectrum CBD.

Synthetic CBD is chemically produced in the laboratory, and as such is also free of THC and other plant compounds. Such laboratory manufacturing processes are conventional. Synthetic CBD and CBD isolate may be generally referred to separately or together as synthetic CBD.

Some examples of cannabidiol derivatives may include cannabidiol acetate and cannabidiol-2',6'-dimethyl ether. Other examples of cannabidiol derivatives may include conjugate molecules formed from an active agent which is linked to a cannabinoid moiety through a specified linker, such as the steroid-cannabinoid conjugates described in PCT publications WO 2020/263888 A1 and WO 2021/076197 A1.

The cannabinoid is present in the compositions/formulations of the present disclosure in a pharmaceutically effective amount. In particular embodiments, the cannabinoid is present in concentrations of from about 3 wt % to about 25 wt %, i.e. about 30 milligram per milliliter (mg/mL) to about 250 mg/mL. In further embodiments, the cannabinoid is present in concentrations of from about 0.1 wt % to about 25 wt %, i.e. about 1 milligram per milliliter (mg/mL) to about 200 mg/m L. In more specific embodiments, the cannabinoid is present in concentrations of from about 0.1 wt % to about 20 wt %, or from about 0.1 wt % to about 15 wt %, or about 0.1 wt % to about 10 wt %, or about 0.1 wt % to about 5 wt %, or about 1 wt % to about 20 wt %, or about 1 wt % to about 15 wt %, or about 1 wt % to about 10 wt %, or about 1 wt % to about 5 wt %. Such concentrations may be suitable for use in cosmeceuticals or nutraceuticals.

In more specific embodiments, the cannabinoid is CBD, which is present in concentrations of about 30 mg/mL to about 250 mg/mL, or about 30 mg/mL or about 60 mg/mL, or about 90 mg/mL, or about 120 mg/mL, or about 150 mg/mL, or about 180 mg/mL, or about 210 mg/mL, or about 250 mg/mL, or in ranges bounded by any two of these values. The cannabinoid in the compositions/formulations of the present disclosure is preferably a cannabinoid derived from natural products having no or low THC content, such as that produced by PureForm Global, Inc., Los Angeles, CA Olive Oil (B) Olive oil is a liquid fat or oil extracted from olives, the fruit of the olive tree, Olea europaea. The oil is separated from the other vegetable material in olives by various types of mechanical or chemical extraction processes, such as by pressing. Olive oil contains mainly high amounts of oleic acid, along with lower amounts of other fatty acids such as linoleic acid and palmitic acid.

Olive oil is believed to contain the following fatty acids in the approximate listed ranges (based on total weight of the oil) in Table 1:

TABLE 1

| Fatty acid | Amount in olive oil (wt %) |
|---|---|
| Palmitic Acid (16:0) | about 7.5 to about 20 |
| Palmitoleic (16:1) | about 0.3 to about 3.5 |
| Stearic acid (18:0) | about 0.5 to about 5 |
| Arachidic Acid (20:0) | 0 to about 0.8 |
| Oleic acid (18:1) | about 55 to about 83 |
| Linoleic acid (18:2) | about 3.5 to about 21 |
| Linolenic acid (18:3) | 0 to about 1.5 |

One measure of olive oil is the weight percent of free oleic acid. In the United States, extra virgin olive oil has a free fatty acid content of 0.8 wt % or less, and virgin olive oil has a free fatty acid content of 2 wt % or less. The grade of the olive oil used in the compositions/formulations of the present disclosure is not believed to be significant other than its suitability for topical use, such as CAS #8001-25-0.

In some embodiments, the olive oil may be modified to comprise at least 0.1 wt % of at least one molecule containing an aliphatic chain with at least one cyclopropyl or cyclopropenyl group. In more particular embodiments, the oil comprises from at least 0.1 wt % to about 12 wt % of the at least one molecule, or at least 0.1 wt % to about 10 wt % of the at least one molecule, including from about 0.5 wt % to about 5 wt %, or from about 1 wt % to about 4 wt %, or a range made from any combination of two of these listed endpoints. Each molecule may be present in an amount within these ranges, or the total amount of such molecules in the oil may be within these ranges.

The term "aliphatic" refers to a hydrocarbon chain which is linear or branched, and which contains at least eight carbon atoms. The carbon atoms of the cyclopropyl or cyclopropenyl group(s) are counted towards the number of carbon atoms in the hydrocarbon chain. The hydrogen atoms on the hydrocarbon chain may be substituted with heteroatom-containing groups such as hydroxyl (—OH) or others, so long as the overall chain remains nonpolar and the molecule is insoluble in water.

Such molecules containing an aliphatic chain with at least one cyclopropyl or cyclopropenyl group may be natural or synthetic. Non-limiting examples of such molecules include sterculic acid, malvalic acid, and dihydrosterculic acid. Such molecules could be artificially synthesized, for example, by reacting an epoxy-containing molecule with a carboxylic acid containing a cyclopropyl group. The carboxylic acid group would react with the epoxy group to obtain a product that contains a hydroxyl group and the cyclopropyl group. In some embodiments, the molecule contains one or two cyclopropyl or cyclopropenyl groups. In particular embodiments, each aliphatic chain contains up to 24 carbon atoms.

In particular embodiments, the molecule containing an aliphatic chain with at least one cyclopropyl or cyclopropenyl group is a cyclopropene fatty acid or a cyclopropane fatty acid (CPFA). The fatty acid includes a carboxylic acid at the end of an aliphatic chain. The fatty acid can be present in the form of a free fatty acid, or as an ester such as a triglyceride, phospholipid, or a cholesteryl ester. The cyclopropene fatty acid(s) are generally mono-unsaturated fatty acids (MUFA), and not poly-unsaturated fatty acids. The cyclopropane fatty acid(s) are generally saturated fatty acids. It is contemplated that the presence of CPFAs may improve the properties of the oil as a carrier for the cannabinoid. Thus, the addition of one or more CPFAs to an oil may result in a "synthetic" olive oil with improved performance.

In more particular embodiments, the olive oil comprises from at least 0.1 wt % to about 12 wt % of the at least one CFPA, or at least 0.1 wt % to about 10 wt % of the at least one CFPA, including from about 0.5 wt % to about 5 wt %, or from about 1 wt % to about 4 wt %, or a range made from any combination of two of these listed endpoints. Each CPFA may be present in an amount within these ranges, or the total amount of CPFAs in the oil may be within these ranges.

In particular embodiments, the CPFA is sterculic acid and/or malvalic acid and/or dihydrosterculic acid. Sterculic acid is 8-(2-octylcycloprop-1-en-1-yl)octanoic acid, and contains a 9,10-cyclopropenyl group. Malvalic acid is 7-(2-octylcycloprop-1-en-1-yl) heptanoic acid, and contains an 8,9-cyclopropenyl group. Dihydrosterculic acid is similar to sterculic acid, but contains a 9,10-cyclopropyl group instead. In some particular embodiments, sterculic acid is present in an amount of about 0.4 wt % to about 6 wt % of the olive oil, or from about 0.4 to about 2 wt % of the olive oil. In other particular embodiments, malvalic acid is present in an amount of about 1 wt % to about 10 wt % of the olive oil, or from about 1 wt % to about 5 wt % of the olive oil. In still further particular embodiments, dihydrosterculic acid is present in an amount of from about 1.5 wt % to about 12 wt % of the olive oil, including from about 1.5 wt % to about 5 wt % of the olive oil. Any combination of two of these acids, or all three of these acids, may also be present in the olive oil, in an amount as listed.

The olive oil may further comprise vaccenic acid and/or heptadecenoic acid. Vaccenic acid is (11E)-octadec-11-enoic acid. In some embodiments, vaccenic acid is present in an amount of about 0.5 wt % to about 3 wt % of the olive oil. In other embodiments, heptadecenoic acid is present in an amount of about 0.1 wt % to about 2 wt % of the olive oil. Both of these acids may also be present in the olive oil, in an amount as listed.

It is contemplated that any combination of the CPFAs, along with vaccenic acid, and/or heptadecenoic acid, could be added to the olive oil to obtain a "synthetic" olive oil that has improved performance. For example, the cannabinoid may be better absorbed through the skin.

The olive oil acts as a solubilizer for the cannabinoid, particularly CBD, and serves as a carrier or vehicle for the cannabinoid. The olive oil is thus present in the compositions/formulations of the present disclosure in an amount sufficient to act as a carrier or vehicle for the cannabinoid. In some embodiments, the olive oil can be present in an amount from about 75 wt % to about 97 wt % of the composition/formulation. In other embodiments, the olive oil is present in an amount of up to 27.75 wt % of the composition, including about 20 wt % to about 27 wt %. or about 5 wt %, or about 6 wt %, or about 8 wt %, or about 10 wt %, or about 12 wt %, or about 14 wt %, or about 15 wt %, or about 16 wt %, or about 18 wt %, or about 20 wt %, or about 22 wt %, or about 24 wt %, or about 25 wt %, or ranges bounded by any two of these values.

Emulsifier

The composition may also include (C) an emulsifier, which stabilizes the mixture by assisting in the mixing of aqueous and organic ingredients. The emulsifier may be a surfactant, which itself may be anionic, nonionic, amphoteric, cationic, and zwitterionic surfactants, or a combination thereof.

Anionic surfactants are well-known to those skilled in the art. Examples include anionic sulfonate or sulfonic acid surfactants, alkylbenzene sulfonates, primary and secondary alkylsulfates, alkyl ether sulfates, and fatty acid ester sulfonates. These surfactants typically have from 9 to 22 carbon atoms. The sulfates can be linear or branched. Other suitable anionic surfactants can include fatty methyl ester sulfonates, alkyl ethyoxy sulfates (AES), and/or alkyl polyalkoxylated carboxylates (AEC). Mixtures are also contemplated. Salt forms of anionic surfactants are also contemplated.

Some examples of nonionic surfactants include alkoxylated nonionic surfactants typically having from 6 to 22 carbon atoms. Such surfactants can be linear, branched, cyclic, or aromatic. Sometimes, the nonionic surfactant is derived from a primary or secondary alcohol. The nonionic surfactants can be "capped," wherein one or more —OH groups are replaced by —OR wherein R is typically C1-C3 alkyl.

Cationic surfactants can also be used. Examples include cationic esters and quaternary ammonium salts of the general formula $R_1R_2R_3R_4N^+X^-$, wherein the R groups are long or short hydrocarbyl chains, typically alkyl, hydroxyalkyl or ethoxylated alkyl groups, and X is a solubilizing group. Other examples of cationic surfactants include alkyltrimethylammonium salts or their hydroxyalkyl substituted analogs. The cationic surfactants can be either water-soluble or water-insoluble.

Examples of amphoteric surfactants include derivatives of aliphatic secondary and tertiary amines such as cocoamphoacetate, cocoamphodiacetate, lauroamphoacetate, lauroamphodiacetate, and mixtures thereof.

Examples of zwitterionic surfactants include derivatives of aliphatic quaternary ammonium, phosphonium, and sulfonium compounds, for example betaines. Amine oxide surfactants may also be used.

In particular embodiments, the emulsifier is sorbitan oleate, a nonionic surfactant with CAS #1338-43-8. Sorbitan oleate is commercially available as SPAN® 80 from Croda International PLC.

The emulsifier is present in the compositions/formulations of the present disclosure in an amount of up to 8 wt % of the composition. In more particular embodiments, the emulsifier is about 1 wt % to about 4 wt % of the composition, or about 2 wt % of the composition.

Diethylene Glycol Monoethyl Ether

The composition may also contain (D) diethylene glycol monoethyl ether, which is CAS #111-90-0, and is also known as TRANSCUTOL®, DGME, or DEGEE. This ingredient is a solvent and solubilizer, and is associated with skin penetration enhancement that aids in topical application of the composition. In other words, this ingredient aids the composition in crossing the skin barrier.

The diethylene glycol monoethyl ether is present in the compositions/formulations of the present disclosure in an amount of up to about 15 wt % of the composition, including about 10 wt % to about 15 wt %, or about 13 wt %.

Polysorbate 80

The composition may also contain (E) polysorbate 80, which is CAS #9005-65-6. This ingredient is also known as TWEEN® 80 or polyoxyethylene (20) sorbitan monooleate. Polysorbate 80 is a nonionic surfactant, and acts as a stabilizer and emulsifier.

The polysorbate 80 is present in the compositions/formulations of the present disclosure in an amount of up to about 4 wt %, including about 1 wt % to about 4 wt %, or about 2 wt %.

Gelling Agent

The composition may also contain (F) a gelling agent or gellant, which aids in the formation of a gel or cream. In particular embodiments, the gelling agent is a formulation containing about 20 wt % to about 40 wt % isohexadecane, with the balance being an acrylamide/acryloyldimethyltaurate copolymer, and polysorbate 80. This formulation is commercially available as Sepineo® P600 from Seppic SA. This formulation also acts as a thickening agent, an emulsifier, and/or a stabilizer. It is stable over a pH of 3 to 11, and is nonthixotropic.

The gelling agent is present in the compositions/formulations of the present disclosure in an amount of up to about 5 wt %, including about 3 wt % to about 5 wt %, and about 4 wt %.

Fatty Alcohol

The composition may also contain (G) at least one fatty alcohol, which can act as an emollient, emulsifier, and/or thickening agent. The fatty alcohol usually contains from 12 to 26 carbon atoms and is typically a primary alcohol. Non-limiting examples of fatty alcohols include lauryl alcohol (C12), cetyl alcohol (C16), stearyl alcohol (C18), and oleyl alcohol (C18). In particular embodiments, the fatty alcohol is cetostearyl alcohol, CAS #67762-27-0, which is a mixture of predominantly cetyl alcohol and stearyl alcohol.

The fatty alcohol(s) is present in the compositions/formulations of the present disclosure in an amount of up to about 8 wt %, including from about 3 wt % to about 5 wt %, and about 4 wt %.

Water

The balance of the compositions/formulations of the present disclosure is (H) water. In particular embodiments, water is present in an amount of about 33 wt % to about 50 wt %, including from about 36 wt % to about 45 wt %.

Additional Ingredients

The compositions/formulations of the present disclosure may include other ingredients besides the ingredients listed above. Such ingredients may include an antioxidant, mineral oil, petrolatum, medium-chain triglycerides (MCT oil), sunflower oil and other components that provide structure or serve as stabilizers, thinners, thickeners, fragrances, moisturizers, emollients and/or ingredients that provide additional anti-irritation or anti-inflammatory properties to the formulation. Some such ingredients are described in this section.

In specific embodiments of the compositions contemplated herein, the composition also includes (I) an antioxidant. In particular embodiments, the antioxidant is butylated hydroxytoluene (BHT), which is CAS #128-37-0. The antioxidant/BHT may be present in the amount of about 0.01 wt %.

When present, the mineral oil is desirably an NF grade light mineral oil, which will not clog the pores of the skin. United States Pharmacopeia (USP) standards should be met.

Petrolatum, aka "petroleum jelly," is useful in topical ointments as a carrier or base, as opposed to water-based cremes or gels. Petrolatum is known to temporarily protect minor cuts, scrapes and burns, and for being effective in keeping skin moist during post-surgery healing. Petrolatum comes in many grades. To the extent that the formulations of the present disclosure uses petrolatum, pharmacy grade petrolatum will be used, such as white petrolatum USP meeting requirements for USP and FDA requirements of 21 CFR 172.880, which are commercially available.

Examples of additional emollients and oils that can be included in the topical formulation are medium-chain triglycerides (MCT oil), sunflower oil, long-chain triglycerides (LCT oil), long-chain fatty acids (e.g., myristic acid, palmitic acid, stearic acid, arachidic acid, linoleic acid), glycerine/glycerol, glycerol monolinoleate, coconut oil, corn oil, canola oil, avocado oil, vegetable oil, flaxseed oil, palm oil, palm kernel oil, peanut oil, rice bran oil, safflower oil, jojoba oil, argan oil, grapeseed oil, castor oil, wheat germ oil, peppermint oil, and sesame oil. It is noted that medium-chain triglycerides are those in which the carbohydrate chain has 8 to 12 carbon atoms. The total amount of any additional oils may be from about 0.5 wt % to about 12 wt %.

Additional fragrances, moisturizers, and emollients may also be variously and preferably included in the formulations disclosed herein, with fragrances typically at concentrations less than about 1 wt %.

In some particular embodiments, the compositions/formulation of the present disclosure comprise a pharmaceutically effective amount of a cannabinoid; and olive oil in an amount sufficient to act as a vehicle for the cannabinoid. The amount of the cannabinoid may be from about 3 wt % to about 25 wt % of the composition. The amount of the olive oil may be from about 75 wt % to about 97 wt % of the composition.

In other particular embodiments, the compositions/formulation of the present disclosure contain: about 3 wt % to about 25 wt % of a cannabinoid; up to 27.75 wt % of olive oil; up to 8 wt % of an emulsifier; up to 15 wt % of diethylene glycol monoethyl ether; up to 4 wt % of polysorbate 80; up to 5 wt % of a gelling agent; up to 8 wt % of a fatty alcohol; and balance water.

In still other particular embodiments, the compositions/formulation of the present disclosure contain: about 3 wt % to about 25 wt % of the cannabinoid; about 20 wt % to about 27 wt % of the olive oil; about 1 wt % to about 4 wt % of the emulsifier; about 10 wt % to about 15 wt % of the diethylene glycol monoethyl ether; about 1 wt % to about 4 wt % of the polysorbate 80; about 3 wt % to about 5 wt % of the gelling agent; about 3 wt % to about 5 wt % of the fatty alcohol; and balance water.

Also particular contemplated are compositions that consist essentially of: from about 3 wt % to about 25 wt % of a cannabinoid; about 27 wt % of olive oil; about 2 wt % of an emulsifier; about 13 wt % of diethylene glycol monoethyl ether; about 2 wt % of polysorbate 80; about 4 wt % of a formulation containing about 20 wt % to about 40 wt % isohexadecane, an acrylamide/acryloyldimethyltaurate copolymer, and polysorbate 80; about 4 wt % of a fatty alcohol; about 0.01 wt % of an antioxidant; and balance water.

Synthesis/Preparation

The compositions/formulations of the present disclosure can be made using methods known in the art. For example, the composition can be made by first mixing the cannabinoid with the olive oil and the diethylene glycol monoethyl ether to dissolve the cannabinoid, usually done at room temperature. The emulsifier and fatty alcohol are then added and mixed at an elevated temperature such as about 55° C. to about 60° C. This oil-phase mixture is then set aside.

Next, an aqueous-phase mixture is made separately by combining water and polysorbate 80, and optional antioxidant if present and mixing. This can also be done at an elevated temperature such as about 55° C. to about 60° C.

The oil-phase mixture and the aqueous-phase mixture are then combined and homogenized to form an emulsion. While mixing, the temperature is reduced. The Sepineo™ P600 (F) is added around 40° C., and mixing is continued until the temperature is reduced to room temperature.

Applications

The compositions/formulations of the present disclosure are intended to be applied topically to the skin of the user/patient. This results in the active ingredient being delivered to local tissue. The formulations may also operate transdermally, delivering the active ingredient across the skin and into systemic circulation.

The topical formulation may be in the form of a cream, gel, hydrogel, liquid, lotion, or ointment. The topical formulation may be applied manually, sprayed, or by syringe, applicator, or other dispensing means. The topical formulation could alternatively be provided in the form of a matrix-type delivery system, where the formulation is absorbed or suspended in a matrix that is then adhered to a backing membrane (commonly referred to as a bandage or a patch).

The topical formulations of the present disclosure desirably have the advantages of efficacy, safety, tolerability, speed of healing, and lowered sensation of pain for the user/patient.

A single formulation may be used to treat or ameliorate radiation dermatitis. This is done by applying the topical formulation to the skin of the user/subject/patient. In some embodiments, the topical formulation is applied after the radiation exposure. The duration of the treatment may be between 24 hours and 14 days. In another example, the duration of the treatment may be between 24 hours and 30 days. In another example, the duration of the treatment is between 1 month to 12 months. With respect to time, the application may be on a regular or irregular schedule, as desired. Generally, the topical formulation is used as needed to ameliorate pain or assist in healing.

In some further embodiments, two different formulations are used together to treat or ameliorate radiation dermatitis. A first formulation comprising a cannabinoid is administered to the patient for a first time period. Subsequently, a second formulation comprising the cannabinoid is administered to the patient for a second time period. The second formulation contains a higher dosage of the cannabinoid than the first formulation. Again, typically, the formulations are made for topical application/administration. The two formulations may be designed to have different permeation rates through the skin, too.

In some specific embodiments, the first formulation contains about 3 wt % of the cannabinoid, and the second formulation contains about 12 wt % of the cannabinoid. In some other specific embodiments, the first formulation contains about 3 wt % to about 12 wt % of the cannabinoid, and the second formulation contains about 12 wt % to about 25 wt % of the cannabinoid (but higher than the first formulation). In other embodiments, the second formulation contains at least 6 wt % (by absolute amt) more of the cannabinoid than the first formulation. For example, if the first formulation contains 3 wt %, the second formulation contains 9 wt % or more. In yet other embodiments, the second formulation contains at least 100% more (relative amt) of the cannabinoid than the first formulation, and up to 400% more. For example, if the first formulation contains 3 wt %, the second formulation contains 6 wt % or more.

The duration of the first time period and the second time period can vary, and do not need to be the same. In some embodiments, the first time period is from about 7 days to about 14 days. In some embodiments, the second time period is from about 7 days to about 14 days. In still other embodiments, the second time period is at least 7 days longer than the first time period.

The present disclosure in a further aspect includes providing a kit comprising the topical composition of the present disclosure; and in a further example providing a kit comprising the topical composition of the present disclosure and any or all of an applicator, such as a pad, utensil, spatula, sprayer or droplet dispenser; and/or a bandage, such as a dermal patch, wrap or other form of bandage and instructions for use thereof.

The present disclosure will further be illustrated in the following non-limiting examples, it being understood that these examples are intended to be illustrative only and that the disclosure is not intended to be limited to the materials, conditions, process parameters and the like recited herein.

EXAMPLES

Example 1

A 3D in vitro skin model containing epidermal keratinocytes and dermal fibroblasts was used. Some tissues were irradiated with 200 mJ UVB/cm$^2$. Test materials were applied topically for 24 hours (after UVB exposure) and an MTT assay was used to check the viability of cells. The following treatment groups were used:
- olive oil (no CBD);
- CBD in olive oil in concentrations of 30, 60, 120, and 250 mg/mL;
- No treatment; and
- Triton-X® as positive control.

Cytotoxicity was assessed with a lactate dehydrogenase (LDH) assay using media collected from the wells of the tissues. Increased LDH activity is an indicator of damaged or dead cells.

The results are provided in the following Table A, with the untreated group defining 0% cytotoxicity and Triton-X defining 100% cytotoxicity. Lower cytotoxicity is better. * indicates $p \leq 0.05$ and ** indicates $p \leq 0.01$ statistical significance after performing unpaired t-test.

TABLE A

| Group | Treatment | UV? | Cytotoxicity (%) |
|---|---|---|---|
| A | Vehicle Control - olive oil only | N | 5 |
| B | 30 mg/mL CBD in olive oil | N | 4 |
| C | 60 mg/mL CBD in olive oil | N | 4 |
| D | 120 mg/mL CBD in olive oil | N | 5 |
| E | 250 mg/mL CBD in olive oil | N | 11 |
| F | Untreated | N | 0 |
| G | 30 mg/mL CBD in olive oil | Y | 17 |
| H | 60 mg/mL CBD in olive oil | Y | 19 |
| I | 120 mg/mL CBD in olive oil | Y | 16 |
| J | 250 mg/mL CBD in olive oil | Y | 16 |
| K | Untreated | Y | 16 |
| L | Triton-X | N | 100 |

All treatment groups exposed to UV had cytotoxicity greater than 10%.

Next, changes in gene expression for 178 genes were measured in tissues. Statistical significance was determined using unpaired t-test, P<0.05, N=4.

First, Group A was compared to Group F, to show the effect of olive oil by itself on gene expression. Seven genes were found to have a linear fold change (FC) of 2 or greater. Those genes were ADRB2, ATP7A, FA2H, MT1F, NOCT, PTGS2, and SERPINH1. FA2H, SERPINH1, and PTGS2 are genes that promote epidermal barrier formation and pain and inflammation. ADRB2, ATP7A, and MT1F are associated with pigmentation of skin. The expression of the NOCT gene was turned on, which plays a role in circadian rhythm regulation.

Second, Group A was compared to Group K, to show the effect of UV exposure by itself on gene expression. FC of 2 or greater was seen in 95 of the tested genes.

Next, Groups G-K were compared to determine the effect of CBD dissolved in olive oil in UV exposed tissues. Group K was used as the baseline. In Group G with 30 mg/mL CBD, the regulated genes were associated with cell renewal, tissue remodeling, anti-apoptotic pathway, and extracellular matrix integrity. In contrast, in Group I 120 mg/mL CBD, the regulated genes were associated with antioxidant/stress response.

Next, Groups A-E were compared to determine the effect of CBD dissolved in olive oil on healthy tissues. Group A was used as the baseline. FC of 2 or greater was seen in only four genes, including IL20RA, IL24, MT1G, and SPINK7.

Example 2

A study was performed on mice to determine the efficacy of topically-dosed CBD in an olive oil vehicle for the treatment of acute radiation-induced dermatitis. Three different CBD dosages were used— 30 mg/mL (3 wt %), 120 mg/mL (12 wt %), and 250 mg/mL (25 wt %).

144 female Balb/c mice with an average starting body weight (±SEM) of 17.96±0.12 grams were randomized into six (6) groups of 24 animals each, as follows:

| Group 1: | Naïve or Control Group |
|---|---|
| Group 2: | 30 Gy only |
| Group 3: | Olive Oil Only |
| Group 4: | 30 mg/mL CBD |
| Group 5: | 120 mg/mL CBD |
| Group 6: | 250 mg/mL CBD |

The control group (Group 1) was not irradiated. The animals in Groups 2-6 were anesthetized via a single intraperitoneal injection of xylazine and ketamine prior to being administered a single dose of 30 Grays (Gy) of radiation directed at a 2 cm×4 cm patch of shaved dorsal skin on Day 0. Radiation was generated by a 160 kVp (15-ma) X-ray source at a focal distance of 10 cm, hardened with a 0.35 mm Cu filtration system at a rate of approximately 3.2 Gy/minute.

The animals were housed by group, 12 per cage. Four animals were euthanized on each of Days 0, 1, and 14, and all remaining animals were euthanized on Day 28. Two of the 24 animals were euthanized due to excess weight loss, inability to eat, or moribundity.

The animals in Groups 1 and 2 did not receive treatment. Dosing for animals in Groups 3-6 began on Day 0 immediately after radiation. Treatments were administered topically (0.1 mL per animal) daily from Days 0-28.

Starting on Day 8 and continuing every other day thereafter (Days 8-28), each animal was evaluated for skin redness and dermatitis, and photographed for subsequent blinded scoring of dermatitis at the completion of the study. Body weight was taken daily.

Skin redness was scored visually by comparison to a photographic scale, and reported on a scale of 0 to 3 in 0.5 unit increments. The scale is described in the table below:

| Score | Description |
|---|---|
| 0 | Normal, no changes |
| 0.5 | Slight erythema, but not normal |

| Score | Description |
|---|---|
| 1 | Mild erythema |
| 1.5 | Mild-moderate erythema |
| 2 | Moderate erythema |
| 2.5 | Moderate-severe erythema |
| 3 | Severe erythema |

Dermatitis was measured by blinded scoring of photographs at the end of the study. Two independent observers graded the photographs, and results were reported on a scale of 0 to 5 in 1.0 unit increments. The scale is described in the table below:

| Score | Description |
|---|---|
| 0 | Normal, no changes |
| 1 | Mild erythema |
| 2 | Moderate to severe erythema, slight desquamation |
| 3 | Desquamation of 25-50% of the irradiated area |
| 4 | Desquamation in >50% of irradiated area |
| 5 | Frank ulcer |

Data were evaluated using one-way ANOVA with Dunnett's multiple comparisons test to compare all groups to the vehicle control group using GraphPad Prism 8.4.3 (La Jolla, CA Duration of dermatitis data was evaluated using the Chi-square test to compare all groups to the vehicle-control group and radiation only group using SigmaPlot 11.0 (Systat Software, Inc.). Statistical significance was achieved when $p<0.05$.

Results

Figure 1:
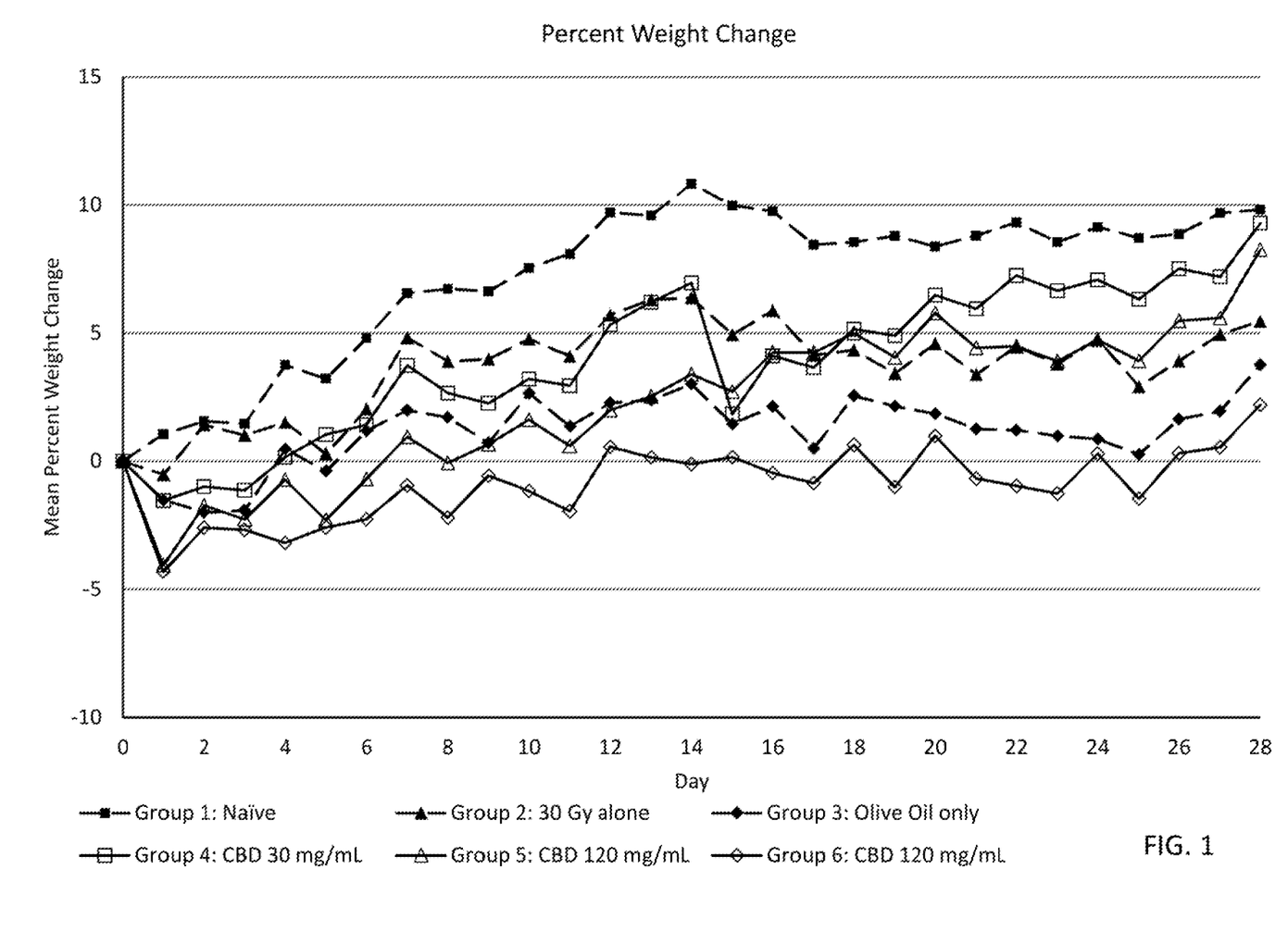
FIG. 1 is a graph showing percent weight change over time for six groups of animals.

FIG. 1 is a graph showing percent weight change over time for the six groups. Generally, the 30 mg/mL and 120 mg/mL CBD-treated groups most closely followed the curve of the naïve group. The differences between the three CBD-treated groups and the other three groups was not found to be statistically significant.

Figure 2:
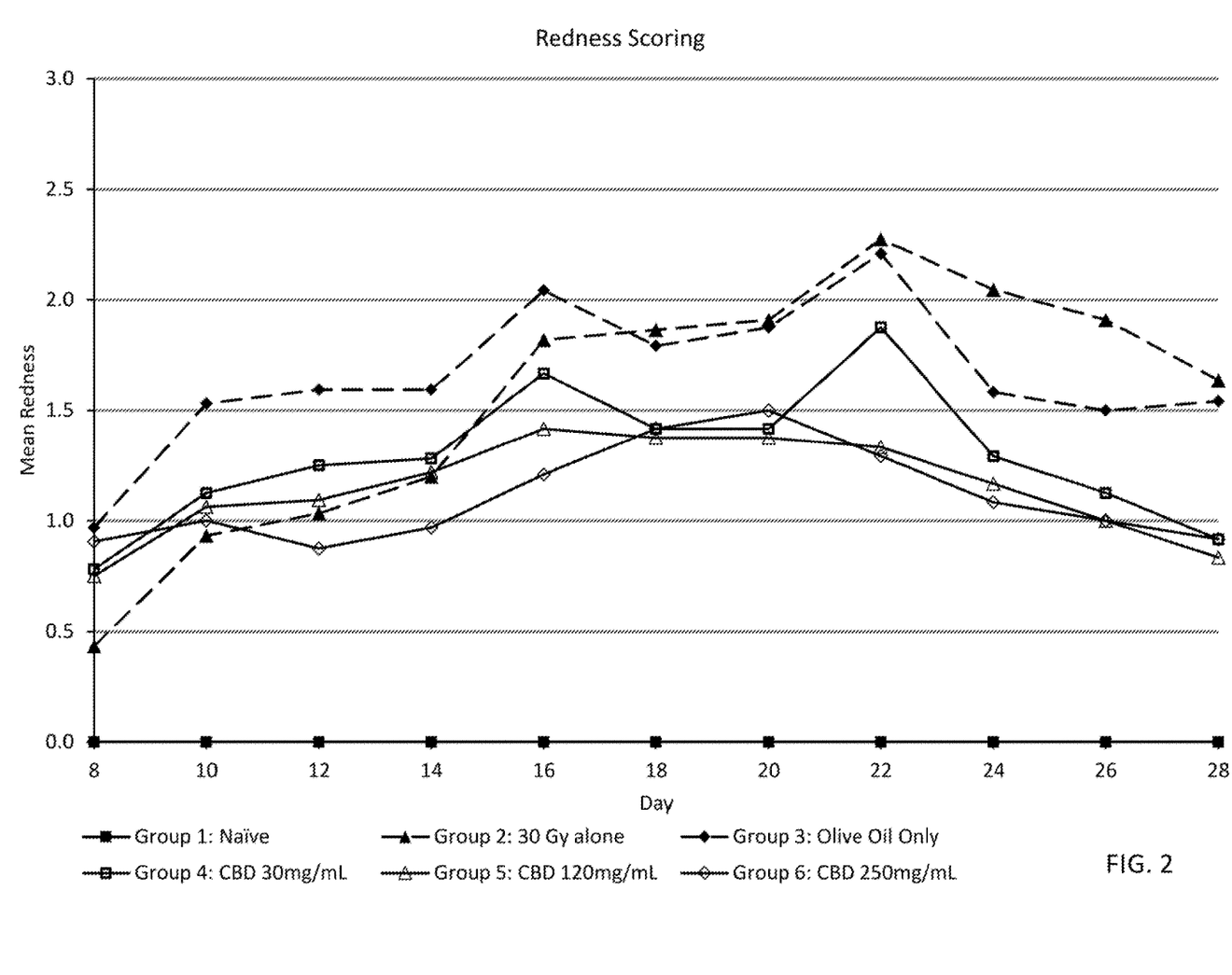
FIG. 2 is a graph showing the redness scoring over time for each group.
Figure 3:
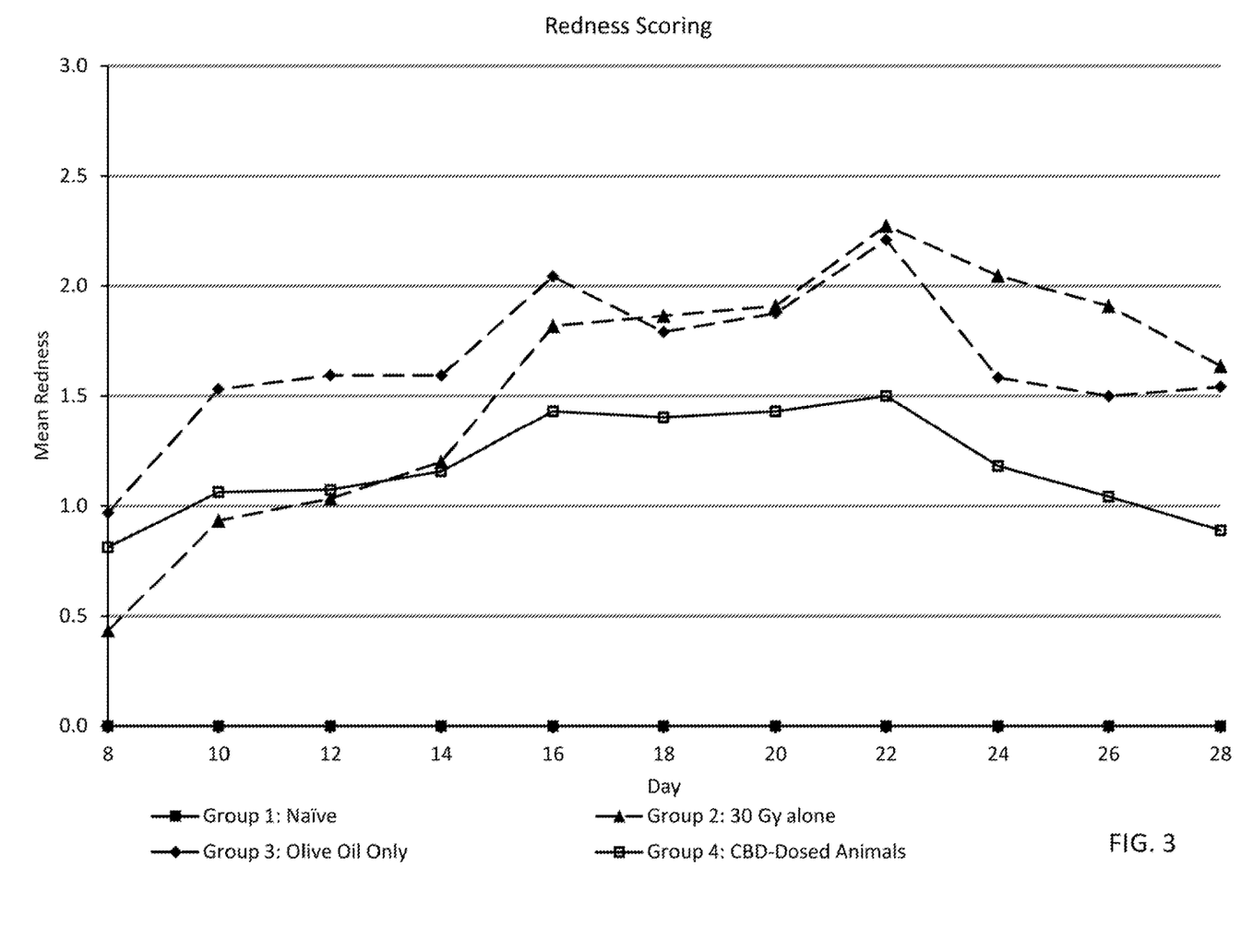
FIG. 3 is a graph showing the redness scoring over time, with the three CBD-treated groups condensed together.

FIG. 2 is a graph showing the redness scoring over time for each group. FIG. 3 is a graph showing the redness scoring over time, with the three CBD-treated groups condensed together. In both graphs, the naïve group (Group 1) had redness score of zero (as expected).

Considered together, the CBD-treated groups had a statistically significant reduction in mean redness scores ($p<0.05$) when compared against Group 2 (radiation only). There was no statistical significance between the three CBD-treated groups. The CBD-treated groups had consistently lower redness scores compared to Group 2 after Day 14, and compared to Group 3 at all time points. This is also shown in the following table:

| | Redness score (mean) | | | | |
|---|---|---|---|---|---|
| | Group 2 (radiation only) | Group 3 (olive oil only) | CBD-treated groups | % Change CBD vs. Group 2 | % Change CBD vs. Group 3 |
| Day 8 | 0.43 | 0.97 | 0.81 | 87.50 | −16.13 |
| Day 10 | 0.93 | 1.53 | 1.06 | 13..84 | −30.61 |
| Day 12 | 1.03 | 1.59 | 1.07 | 3.83 | −32.68 |
| Day 14 | 1.20 | 1.59 | 1.16 | −3.65 | −27.45 |
| Day 16 | 1.82 | 2.04 | 1.43 | −21.32 | −29.93 |
| Day 18 | 1.86 | 1.79 | 1.40 | −24.73 | −21.71 |
| Day 20 | 1.91 | 1.88 | 1.43 | −25.07 | −23.70 |
| Day 22 | 2.27 | 2.21 | 1.50 | −34.00 | −32.08 |
| Day 24 | 2.05 | 1.58 | 1.18 | −42.28 | −25.44 |
| Day 26 | 1.91 | 1.50 | 1.04 | −45.44 | −30.56 |
| Day 28 | 1.64 | 1.54 | 0.89 | −45.68 | −42.34 |

Figure 4:
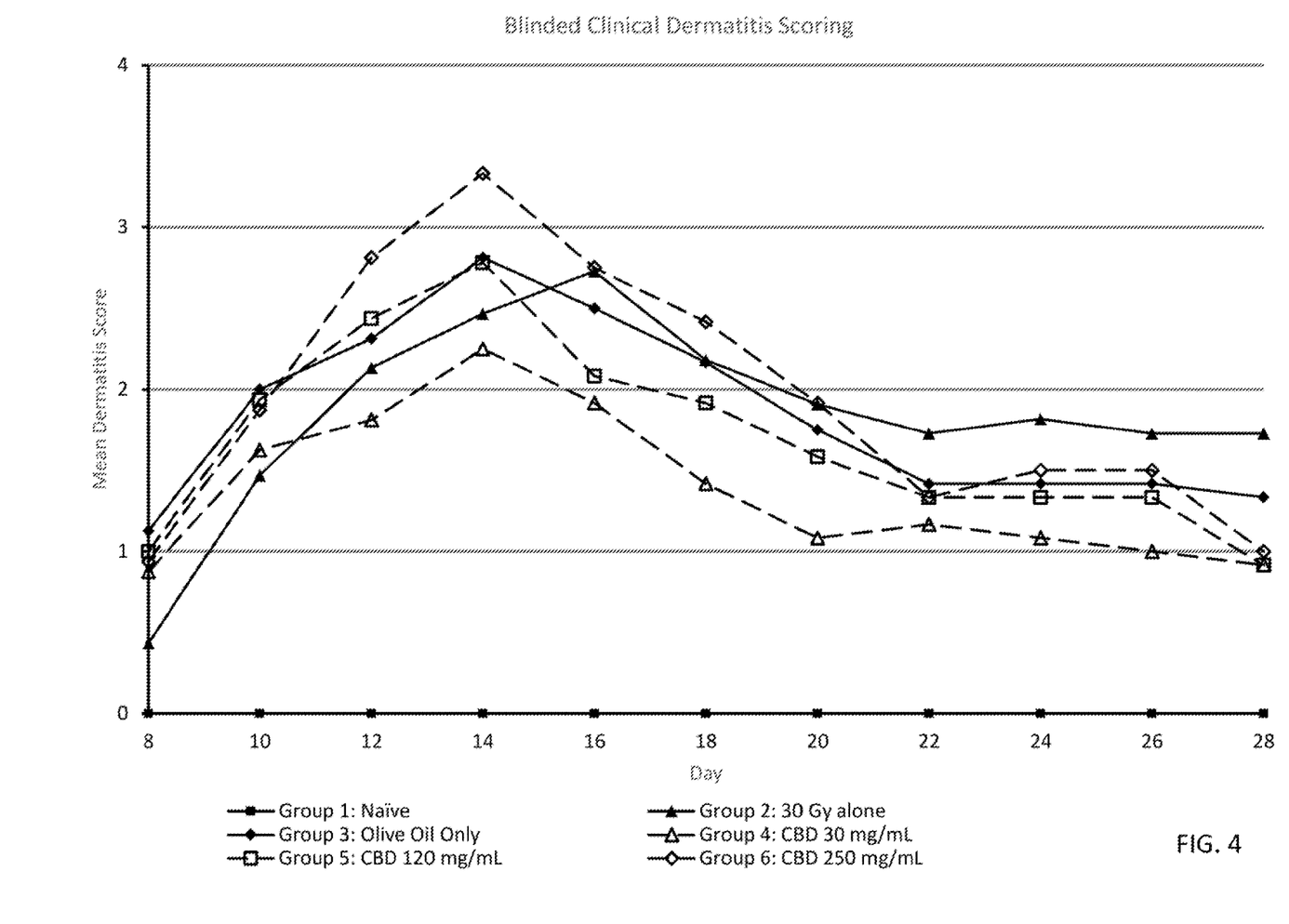
FIG. 4 is a graph showing the blinded clinical dermatitis scoring over time for each group.
Figure 5:
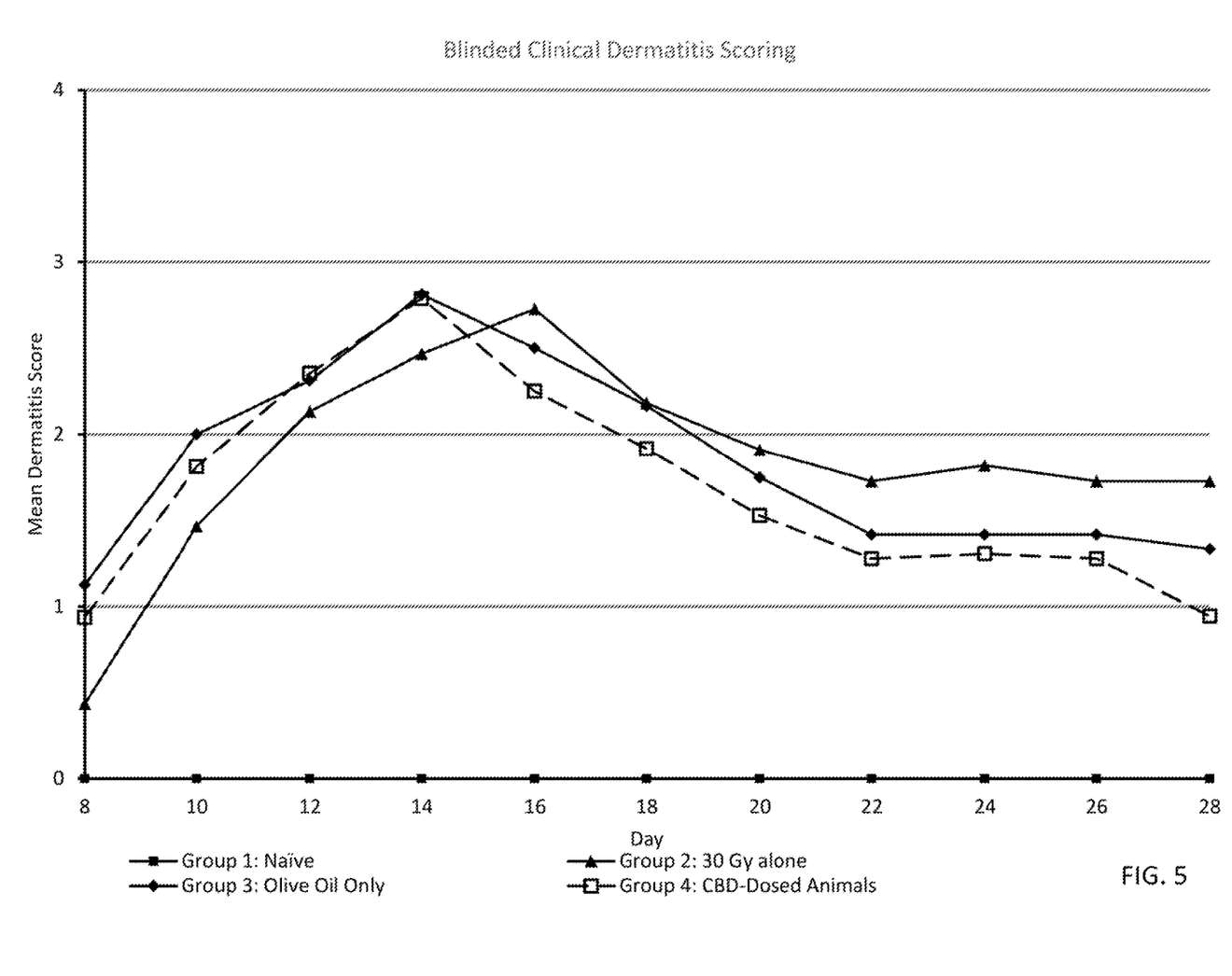
FIG. 5 is a graph showing the blinded clinical dermatitis over time, with the three CBD-treated groups condensed together.

FIG. 4 is a graph showing the blinded clinical dermatitis scoring over time for each group. FIG. 5 is a graph showing the blinded clinical dermatitis over time, with the three CBD-treated groups condensed together. Again, in both graphs, the naïve group (Group 1) had a dermatitis score of zero (as expected).

The 30 mg/mL CBD animals (Group 4) demonstrated consistently decreased mean dermatitis scores when compared against Group 2 (radiation only) and Group 3 (olive oil only). This is also seen in the following table:

| | Dermatitis score (mean) | | | | |
|---|---|---|---|---|---|
| | Group 2 (radiation only) | Group 3 (olive oil only) | Group 4 (30 mg/ mL CBD) | % Change Group 4 vs. Group 2 | % Change Group 4 vs. Group 3 |
| Day 8 | 0.43 | 1.13 | 0.88 | 101.92 | −22.22 |
| Day 10 | 1.47 | 2.00 | 1.63 | 10.80 | −18.75 |
| Day 12 | 2.13 | 2.31 | 1.81 | −15.04 | −21.62 |
| Day 14 | 2.47 | 2.81 | 2.25 | −8.78 | −20.00 |
| Day 16 | 2.73 | 2.50 | 1.92 | −29.72 | −23.33 |
| Day 18 | 2.18 | 2.17 | 1.42 | −35.07 | −34.62 |
| Day 20 | 1.91 | 1.75 | 1.08 | −43.25 | −38.10 |
| Day 22 | 1.73 | 1.42 | 1.17 | −32.46 | −17.65 |
| Day 24 | 1.82 | 1.42 | 1.08 | −40.42 | −23.53 |
| Day 26 | 1.73 | 1.42 | 1.00 | −42.11 | −29.41 |
| Day 28 | 1.73 | 1.33 | 0.92 | −46.93 | −31.25 |

The following table provides information on the duration of moderate dermatitis, which is defined as the number of days on which scores were at least 2

| Treatment | Days ≥2 | Days <2 | Total Animal Days | % Days ≥2 | Chi Sq value vs. Group 2 | p value | Chi Sq value vs. Group 2 | p value |
|---|---|---|---|---|---|---|---|---|
| Naïve | 0 | 137 | 137 | 0.00 | 164.415 | <0.001 | 124.944 | <0.001 |
| 30 Gy only | 104 | 33 | 137 | 75.91 | — | — | 5.102 | 0.024 |
| Olive oil only | 93 | 55 | 148 | 62.84 | 5.102 | 0.024 | — | — |
| 30 mg/mL CBD | 75 | 73 | 148 | 50.68 | 18.332 | <0.001 | 3.978 | 0.046 |
| 120 mg/mL CBD | 88 | 60 | 148 | 59.46 | 8.028 | 0.005 | 0.228 | 0.633 |
| 150 mg/mL CBD | 90 | 57 | 147 | 61.22 | 6.405 | 0.011 | 0.0274 | 0.869 |

The irradiated animals (Group 2) had a significantly higher percentage of days with moderate dermatitis compared to the Olive oil only group (Group 3).

All CBD-treated groups (Groups 4, 5, 6) had a significantly lower percentage of days with moderate dermatitis compared to the irradiated group (Group 2).

The 30/mg/mL CBD group (Group 4) had a significantly lower percentage of days with moderate dermatitis compared to the Olive oil only group (Group 3).

To show how treatment impacted the dermatitis score over time, the following two tables were made to compare the percentage of animals exhibiting moderate dermatitis (score≥2) and severe dermatitis (score≥3) in each treatment group, compared to the Olive oil only group (Group 3). Bold values indicate a decrease (improvement), and underlined values indicate an increase (worsening).

| Percentage of Animals with Moderate Dermatitis (≥2) by day | | | | | | | | | | | |
|---|---|---|---|---|---|---|---|---|---|---|---|
| Treatment | 8 | 10 | 12 | 14 | 16 | 18 | 20 | 22 | 24 | 26 | 28 |
| Naïve | 0 | 0 | 0 | 0 | 0 | 0 | 0 | 0 | 0 | 0 | 0 |
| 30 Gy only | 6.7 | 60 | 100 | 100 | 100 | 100 | 81.8 | 72.7 | 81.8 | 72.7 | 72.7 |
| Olive oil only | 25 | 75 | 87.5 | 100 | 83.3 | 83.3 | 58.3 | 41.7 | 41.7 | 41.7 | 41.7 |
| 30 mg/mL CBD | 18.8 | 75 | 81.3 | 75 | 75 | 66.7 | 33.3 | 47.7 | 33.3 | 25 | 16.7 |
| 120 mg/mL CBD | 18.8 | 87.5 | 93.8 | 100 | 83.3 | 83.3 | 58.3 | 33.3 | 33.3 | 33.3 | 8.3 |
| 250 mg/mL CBD | 12.5 | 75 | 100 | 93.8 | 93.7 | 83.3 | 66.7 | 33.3 | 50 | 50 | 0 |

| Percentage of Animals with Moderate Dermatitis (≥3) by day | | | | | | | | | | | |
|---|---|---|---|---|---|---|---|---|---|---|---|
| Treatment | 8 | 10 | 12 | 14 | 16 | 18 | 20 | 22 | 24 | 26 | 28 |
| Naïve | 0 | 0 | 0 | 0 | 0 | 0 | 0 | 0 | 0 | 0 | 0 |
| 30 Gy only | 0 | 0 | 13.3 | 46.7 | 63.6 | 18.2 | 9.1 | 0 | 0 | 0 | 0 |
| Olive oil only | 0 | 25 | 43.8 | 75 | 66.7 | 33.3 | 16.7 | 0 | 0 | 0 | 0 |
| 30 mg/mL CBD | 0 | 6.3 | 18.8 | 56.3 | 41.7 | 0 | 0 | 0 | 0 | 0 | 0 |
| 120 mg/mL CBD | 0 | 6.3 | 50 | 75 | 25 | 8.3 | 0 | 0 | 0 | 0 | 0 |
| 250 mg/mL CBD | 6.3 | 12.5 | 62.5 | 93.3 | 75 | 58.3 | 25 | 0 | 0 | 0 | 0 |

The 30 mg/mL group (Group 4) had reduced percentages of animals with moderate or severe dermatitis for the majority of surveyed days.

Comparative Example 1

Several other formulations were prepared and tested for color, stability, and viscosity before selecting the formulations to be used. A summary of the ingredients in those formulations, and their results, is provided below:

| Prototype 2A1c | | | | |
|---|---|---|---|---|
| Excipient | Function | 12% w/w | 3% w/w | Results |
| CBD | Active | 12 | 3 | Yellow color |
| Olive Oil | Solubilizer | 40 | 40 | |
| Transcutol | Solvent/solubilizer | 22 | 31 | |
| Simaline L80 | Emulsifier | 2 | 2 | |
| Sepenio P600 | Gelling agent | 4 | 4 | |
| Cetyl alcohol | Emollient/emulsifier/thickener | 5 | 5 | |
| Stearyl alcohol | Emollient/emulsifier | 5 | 5 | |
| GMSII | Viscosifier/Moisturizer | 10 | 10 | |

| Prototype 2A1d | | | | |
|---|---|---|---|---|
| Excipient | Function | 12% w/w | 3% w/w | Results |
| CBD | Active | 12 | 3 | Yellow color |
| Olive Oil | Solubilizer | 40 | 40 | |
| Transcutol | Solvent/solubilizer | 15 | 15 | |
| Sepenio P600 | Gelling agent | 4 | 4 | |
| Cetyl alcohol | Emollient/emulsifier/thickener | 3 | 3 | |
| Stearyl alcohol | Emollient/emulsifier | 3 | 3 | |
| GMSII | Viscosifier/Moisturizer | 5 | 5 | |
| PEG 400 | Solvent | 18 | 27 | |

| Prototype 2A1e | | | | |
|---|---|---|---|---|
| Excipient | Function | 12% w/w | 3% w/w | Results |
| CBD | Active | 12 | 3 | White color |
| Olive Oil | Solubilizer | 30 | 30 | |
| Span 80 | Surfactant/emulsifier | 2 | 2 | |
| Transcutol | Solvent/solubilizer | 10 | 10 | |
| Tween 80 | Emulsifier | 2 | 2 | |
| Sepenio P600 | Gelling agent | 4 | 4 | |
| Cetostearyl alcohol | Emollient/emulsifier/thickener | 4 | 4 | |
| Water | Solvent | 36 | 45 | |

| Prototype 2A1f | | | | |
|---|---|---|---|---|
| Excipient | Function | 12% w/w | 3% w/w | Results |
| CBD | Active | 12 | 3 | White color |
| Olive Oil | Solubilizer | 30 | 30 | |
| Span 80 | Surfactant/emulsifier | 2 | 2 | |
| Transcutol | Solvent/solubilizer | 10 | 10 | |
| Tween 80 | Emulsifier | 2 | 2 | |
| HPC | Gelling agent | 3 | 3 | |
| Water | Solvent | 41 | 50 | |

Prototype 2A1g

| Excipient | Function | 12% w/w | 3% w/w | Results |
|---|---|---|---|---|
| CBD | Active | 12 | 3 | White color |
| Olive Oil | Solubilizer | 30 | 30 | Unstable under |
| Span 80 | Surfactant/emulsifier | 2 | 2 | accelerated |
| Transcutol | Solvent/solubilizer | 10 | 10 | temperature, |
| Tween 80 | Emulsifier | 2 | 2 | leading to |
| Poloxomer 407 | Gelling agent | 1 | 1 | phase |
| Cetostearyl alcohol | Emollient/emulsifier/thickener | 5 | 5 | separation |
| Water | Solvent | 33 | 42 | |
| Glycerin | Solvent | 5 | 5 | |

Prototype 2A

| Excipient | Function | 12% w/w | 3% w/w | Results |
|---|---|---|---|---|
| CBD | Active | 12 | 3 | Dry, soft, non-cohesive |
| Olive Oil | Solubilizer | 40 | 40 | |
| Propylene glycol | Solvent/solubilizer | 14 | 23 | |
| Span 80 | Emulsifier | 2 | 2 | |
| Cetyl alcohol | Emollient/emulsifier/thickener | 5 | 5 | |
| Stearyl alcohol | Emollient/emulsifier | 5 | 5 | |
| GMSII | Viscosifier/Moisturizer | 20 | 20 | |
| Bees Wax | Viscosifier/Moisturizer | 2 | 2 | |

Prototype 2B

| Excipient | Function | 12% w/w | 3% w/w | Results |
|---|---|---|---|---|
| CBD | Active | 12 | 3 | Dry, non-cohesive |
| Olive Oil | Solubilizer | 40 | 40 | |
| Propylene glycol | Solvent/solubilizer | 13 | 22 | |
| Span 80 | Emulsifier | 2 | 2 | |
| Cetyl alcohol | Emollient/emulsifier/thickener | 5 | 5 | |
| Stearyl alcohol | Emollient/emulsifier | 5 | 5 | |
| GMSII | Viscosifier/Moisturizer | 20 | 20 | |
| Bees Wax | Viscosifier/Moisturizer | 2 | 2 | |
| Lecithin | Viscosifier | 1 | 1 | |

Prototype 2B

| Excipient | Function | 12% w/w | 3% w/w | Results |
|---|---|---|---|---|
| CBD | Active | 12 | 3 | Dry, non-cohesive |
| Olive Oil | Solubilizer | 40 | 40 | |
| PEG 3350 | Solvent/solubilizer | 14 | 23 | |
| Span 80 | Emulsifier | 4 | 4 | |
| Cetyl alcohol | Emollient/emulsifier/thickener | 5 | 5 | |
| Stearyl alcohol | Emollient/emulsifier | 5 | 5 | |
| GMSII | Viscosifier/Moisturizer | 20 | 20 | |

Prototype 2A1

| Excipient | Function | 12% w/w | 3% w/w | Results |
|---|---|---|---|---|
| CBD | Active | 12 | 3 | Yellow color |
| Olive Oil | Solubilizer | 50 | 50 | Soft, needs to |
| Propylene glycol | Solvent/solubilizer | 15.5 | 24.5 | be optimized for semi-solid |
| Span 80 | Emulsifier | 2 | 2 | consistency |
| HPC | Gelling agent | 0.5 | 0.5 | |
| Cetyl alcohol | Emollient/emulsifier/thickener | 5 | 5 | |
| Stearyl alcohol | Emollient/emulsifier | 5 | 5 | |
| GMSII | Viscosifier/Moisturizer | 10 | 10 | |

Prototype 2A2

| Excipient | Function | 12% w/w | 3% w/w | Results |
|---|---|---|---|---|
| CBD | Active | 12 | 3 | Yellow color |
| Olive Oil | Solubilizer | 40 | 40 | Dry, solid |
| Propylene glycol | Solvent/solubilizer | 25 | 34 | |
| Span 80 | Emulsifier | 2 | 2 | |
| Cetyl alcohol | Emollient/emulsifier/thickener | 5 | 5 | |
| Stearyl alcohol | Emollient/emulsifier | 5 | 5 | |
| GMSII | Viscosifier/Moisturizer | 10 | 10 | |
| Emulsifying wax | Viscosifier/Moisturizer | 1 | 1 | |

Prototype 2A1a

| Excipient | Function | 12% w/w | 3% w/w | Results |
|---|---|---|---|---|
| CBD | Active | 12 | 3 | Yellow color |
| Olive Oil | Solubilizer | 50 | 50 | |
| Propylene glycol | Solvent/solubilizer | 20.5 | 29.5 | |
| Span 80 | Emulsifier | 2 | 2 | |
| HPC | Gelling agent | 0.5 | 0.5 | |
| Cetyl alcohol | Emollient/emulsifier/thickener | 5 | 5 | |
| Stearyl alcohol | Emollient/emulsifier | 5 | 5 | |
| GMSII | Viscosifier/Moisturizer | 5 | 5 | |

Prototype 2A1b

| Excipient | Function | 12% w/w | 3% w/w | Results |
|---|---|---|---|---|
| CBD | Active | 12 | 3 | Yellow color |
| Olive Oil | Solubilizer | 50 | 50 | |
| Propylene glycol | Solvent/solubilizer | 24.5 | 33.5 | |
| Span 80 | Emulsifier | 2 | 2 | |
| HPC | Gelling agent | 0.5 | 0.5 | |
| Cetyl alcohol | Emollient/emulsifier/thickener | 3 | 3 | |
| Stearyl alcohol | Emollient/emulsifier | 3 | 3 | |
| GMSII | Viscosifier/Moisturizer | 5 | 5 | |

| Prototype P1 | | | |
|---|---|---|---|
| Excipient | Function | 25% w/w | Results |
| CBD | Active | 25 | Yellow color |
| Olive Oil | Solubilizer | 50 | |
| Propylene glycol | Solvent/solubilizer | 10 | |
| Myglyol 840 | Solvent/emollient | 9.5 | |
| Polysorbate 80 | Emulsifier | 2 | |
| Span 80 | Emulsifier | 2 | |
| Hydroxypropyl cellulose | Hydrogel polymer | 1.5 | |

| Prototype P2 | | | |
|---|---|---|---|
| Excipient | Function | 25% w/w | Results |
| CBD | Active | 25 | Yellow color |
| Olive Oil | Solubilizer | 40 | |
| Propylene glycol | Solvent/solubilizer | 16 | |
| Oleic acid | Solvent/emollient | 5 | |
| Span 80 | Emulsifier | 2 | |
| Cetyl alcohol | Emollient/emulsifier/thickener | 5 | |
| Stearyl alcohol | Emollient/emulsifier | 5 | |
| Bees Wax | Viscosifier/Moisturizer | 2 | |

| Prototype P3 | | | | |
|---|---|---|---|---|
| Excipient | Function | 12% w/w | 3% w/w | Results |
| CBD | Active | 12 | 3 | Brown color |
| Olive Oil | Solubilizer | 50 | 59 | |
| VersaGel | Solvent/emollient | 38 | 38 | |

SIMALINE L80 is a mixture of sorbitan oleate and PEG-30 dipolyhydroxystearate, CAS #s 1338-43-8 and 70142-34-6. HPC is hydroxypropyl cellulose. Poloxomer 407 is a triblock copolymer of with a central block of polypropylene glycol flanked by two blocks of polyethylene glycol, and is CAS #691397-13-4.

The present disclosure has been described with reference to exemplary embodiments. Modifications and alterations will occur to others upon reading and understanding the preceding detailed description. It is intended that the present disclosure be construed as including all such modifications and alterations insofar as they come within the scope of the appended claims or the equivalents thereof.

The invention claimed is:

1. A composition for the topical treatment of radiation dermatitis, comprising:
   0.1 wt % to 25 wt % of a cannabinoid;
   about 20 wt % to 27.75 wt % of olive oil;
   wherein the olive oil is modified to comprise at least 0.1 wt % of at least one molecule containing an aliphatic chain with at least one cyclopropyl or cyclopropenyl group;
   1 wt % to 8 wt % of an emulsifier which is a surfactant;
   10 wt % to 15 wt % of diethylene glycol monoethyl ether;
   1 wt % to 4 wt % of polysorbate 80;
   3 wt % to 5 wt % of a gelling agent;
   3 wt % to 8 wt % of a fatty alcohol; and
   balance water.

2. The composition of claim 1, wherein the cannabinoid is a cannabidiol, cannabigerol, cannabichromene, tetrahydrocannabinol, cannabicyclol, cannabielsoin, cannabinol, cannabinodiol, cannabitriol, dehydrocannabifuran, cannabifuran, cannabichromanon, or cannabiripsol, or a derivative thereof.

3. The composition of claim 2, wherein the derivative is an acetylated derivative, a methylated derivative, or a salt of the cannabinoid.

4. The composition of claim 1, wherein the emulsifier which is a surfactant is sorbitan oleate.

5. The composition of claim 1, wherein the gelling agent is a formulation containing about 20 wt % to about 40 wt % isohexadecane, an acrylamide/acryloyldimethyltaurate copolymer, and additional polysorbate 80.

6. The composition of claim 1, wherein the fatty alcohol is cetostearyl alcohol.

7. The composition of claim 1, containing about 33 wt % to about 50 wt % of water.

8. The composition of claim 1, further comprising about 0.01 wt % of an antioxidant.

9. The composition of claim 8, wherein the antioxidant is butylated hydroxytoluene (BHT).

10. The composition of claim 1, wherein the at least one molecule containing an aliphatic chain with at least one cyclopropyl or cyclopropenyl group is a cyclopropene fatty acid or cyclopropane fatty acid (CPFA).

11. The composition of claim 10, wherein the cyclopropene fatty acid or cyclopropane fatty acid is sterculic acid or malvalic acid.

12. The composition of claim 11, wherein the olive oil comprises from about 0.4 wt % to about 6 wt % of sterculic acid or from about 1 wt % to about 10 wt % of malvalic acid.

13. The composition of claim 1, wherein the at least one molecule containing an aliphatic chain with at least one cyclopropyl or cyclopropenyl group is dihydrosterculic acid, which is present in an amount of from about 1 wt % to about 5 wt % of the olive oil.

14. The composition of claim 1, wherein the olive oil further comprises vaccenic acid or heptadecenoic acid.

15. The composition of claim 14, wherein the olive oil contains from about 0.5 wt % to about 3 wt % of vaccenic acid, or from about 0.1 wt % to about 2 wt % of heptadecenoic acid.

16. A method for treating a patient exhibiting radiation dermatitis, comprising:
   administering to an area exhibiting radiation dermatitis a formulation comprising a cannabinoid to the patient;
   wherein the first formulation comprises:
      0.1 wt % to 25 wt % of a cannabinoid;
      about 20 wt % to 27.75 wt % of olive oil;
   wherein the olive oil is modified to comprise at least 0.1 wt % of at least one molecule containing an aliphatic chain with at least one cyclopropyl or cyclopropenyl group;
      1 wt % to 8 wt % of an emulsifier which is a surfactant;
      10 wt % to 15 wt % of diethylene glycol monoethyl ether;
      1 wt % to 4 wt % of polysorbate 80;
      3 wt % to 5 wt % of a gelling agent;
      3 wt % to 8 wt % of a fatty alcohol; and
      balance water.

* * * * *